(12) United States Patent
White et al.

(10) Patent No.: US 7,255,710 B2
(45) Date of Patent: Aug. 14, 2007

(54) HELICAL STENT WITH MICRO-LATCHES

(75) Inventors: Jason White, Atlanta, GA (US); David Stern, Grayson, GA (US); Mark Allen, Atlanta, GA (US); David O'Brien, Norcross, GA (US)

(73) Assignee: ICON Medical Corp., Cleveland, OH (US)

( * ) Notice: Subject to any disclaimer, the term of this patent is extended or adjusted under 35 U.S.C. 154(b) by 646 days.

(21) Appl. No.: 10/636,323

(22) Filed: Aug. 6, 2003

(65) Prior Publication Data

US 2004/0093076 A1    May 13, 2004

Related U.S. Application Data

(60) Provisional application No. 60/401,379, filed on Aug. 6, 2002.

(51) Int. Cl.
*A61F 2/06* (2006.01)

(52) U.S. Cl. .................................... 623/1.15

(58) Field of Classification Search ............... 606/191, 606/192, 194, 198, 195; 623/1.11, 1.12, 623/1.15, 1.2, 1.44
See application file for complete search history.

(56) References Cited

U.S. PATENT DOCUMENTS

| | | | |
|---|---|---|---|
| 4,776,337 A | 10/1988 | Palmaz | |
| 5,306,286 A | 4/1994 | Stack et al. | |
| 5,411,549 A | 5/1995 | Peters | |
| 5,437,311 A * | 8/1995 | Reynolds | 138/115 |
| 5,441,515 A | 8/1995 | Khosravi et al. | |
| 5,582,616 A * | 12/1996 | Bolduc et al. | 606/143 |
| 5,618,299 A | 4/1997 | Khosravi et al. | |
| 5,725,549 A * | 3/1998 | Lam | 623/1.15 |
| 5,741,293 A | 4/1998 | Wijay | |
| 5,824,053 A * | 10/1998 | Khosravi et al. | 623/1.15 |
| 5,976,182 A | 11/1999 | Cox | |
| 6,033,436 A | 3/2000 | Steinke et al. | |
| 6,083,258 A | 7/2000 | Yadav | |
| 2001/0044651 A1 | 11/2001 | Steinke et al. | |

* cited by examiner

*Primary Examiner*—Kevin T. Truong
(74) *Attorney, Agent, or Firm*—Fay Sharpe LLP; Brian E. Turung

(57) ABSTRACT

A stent constructed using elements containing micro-mechanical latching mechanisms is disclosed. The micro-mechanical latching elements allow sliding motion between two surfaces in one direction, and restrict sliding motion in the opposite direction. The micro-mechanical latch surface features are formed using microelectronic mechanical systems (MEMS) manufacturing methods. The male surface of the latching components contains an array of ridges or protrusions, and the receiving surface contains a matching array of recesses. The array of ridges or protrusions and the corresponding recesses have uniformly dissimilar slopes that result in a substantially greater frictional force in one direction than in the opposite direction. The separation distance between the two surfaces is such that the male latch surface is engaged with the receiving surface recesses in the low stress "locked" state, preventing motion in the undesired direction.

50 Claims, 13 Drawing Sheets

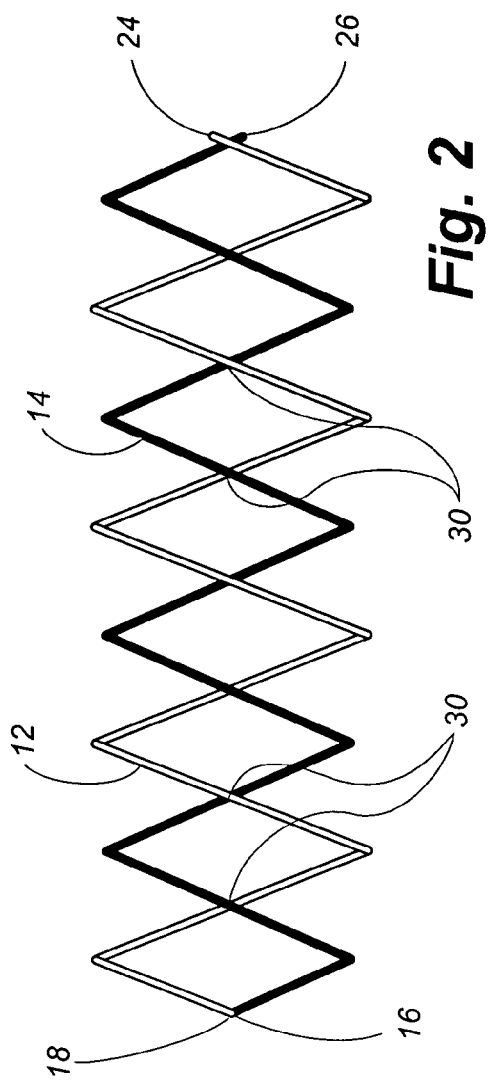
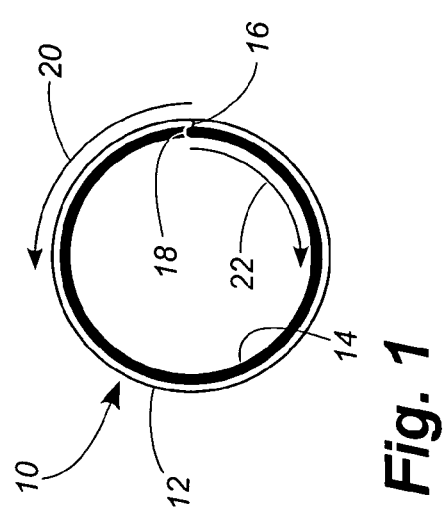
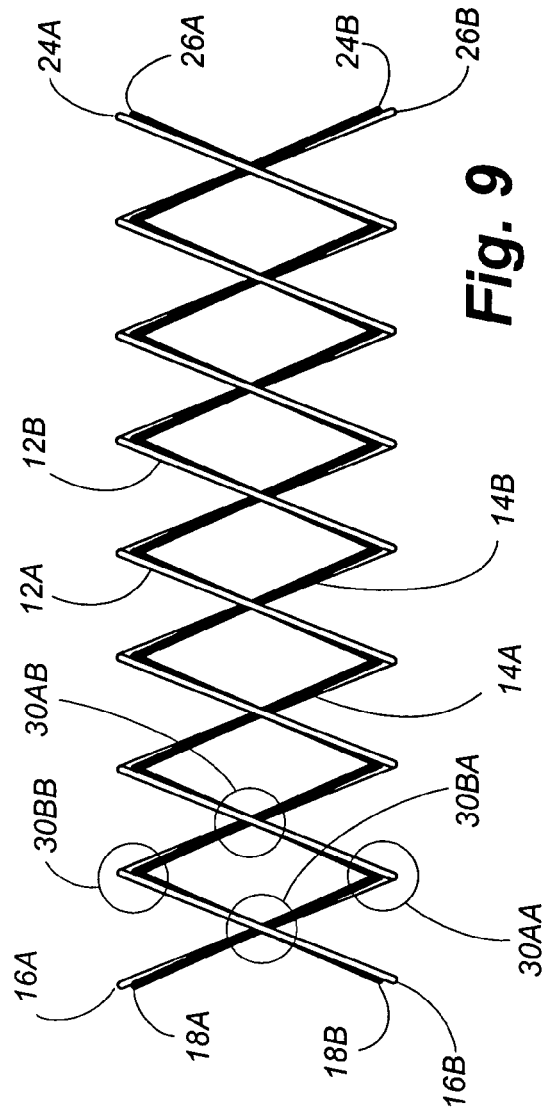
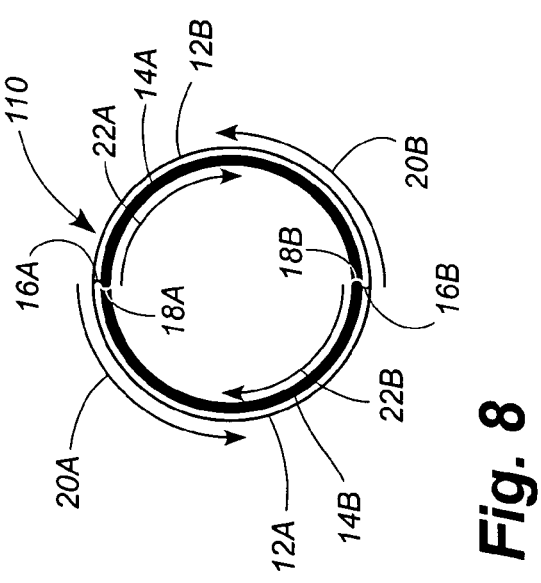
Fig. 2
Fig. 1
Fig. 9
Fig. 8

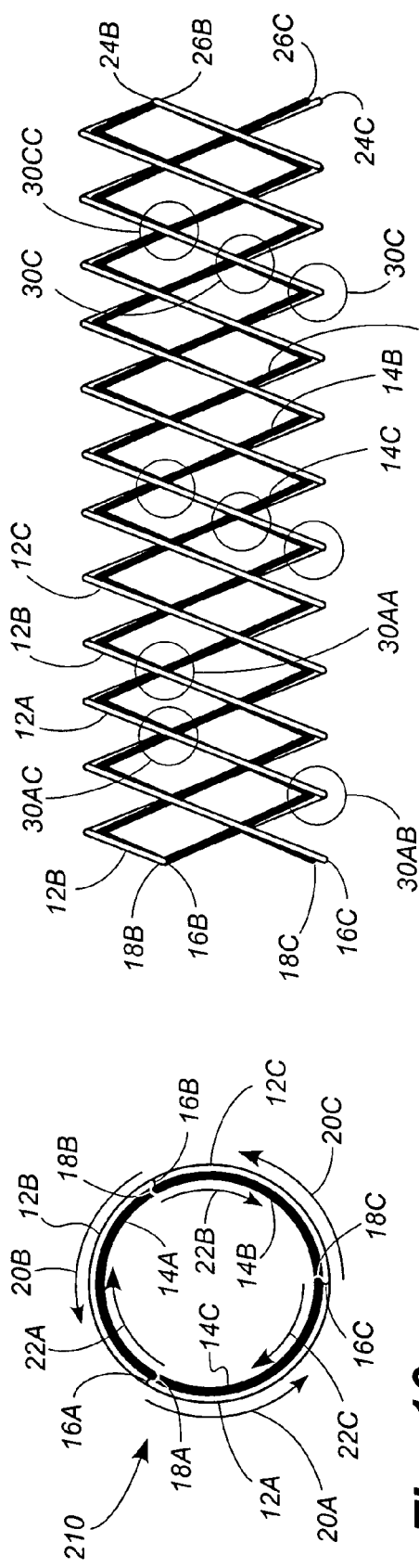
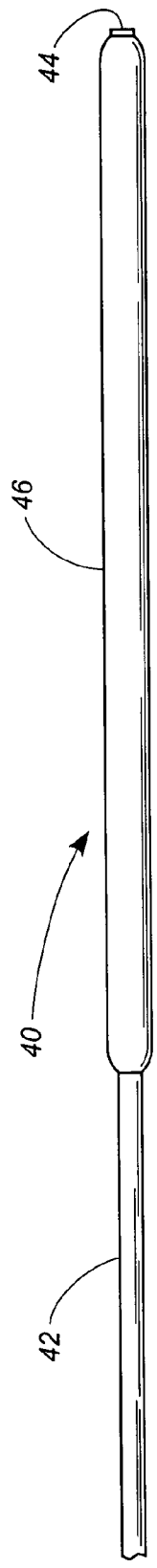
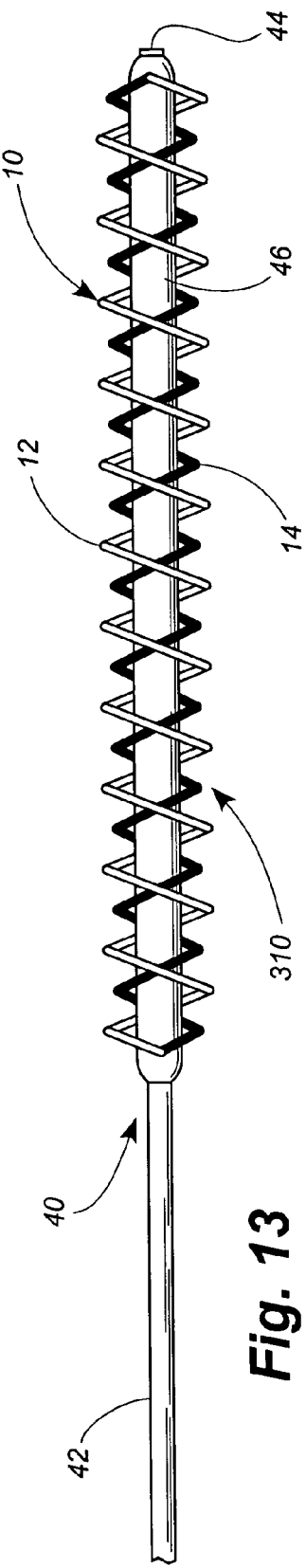
Fig. 10
Fig. 11
Fig. 12
Fig. 13

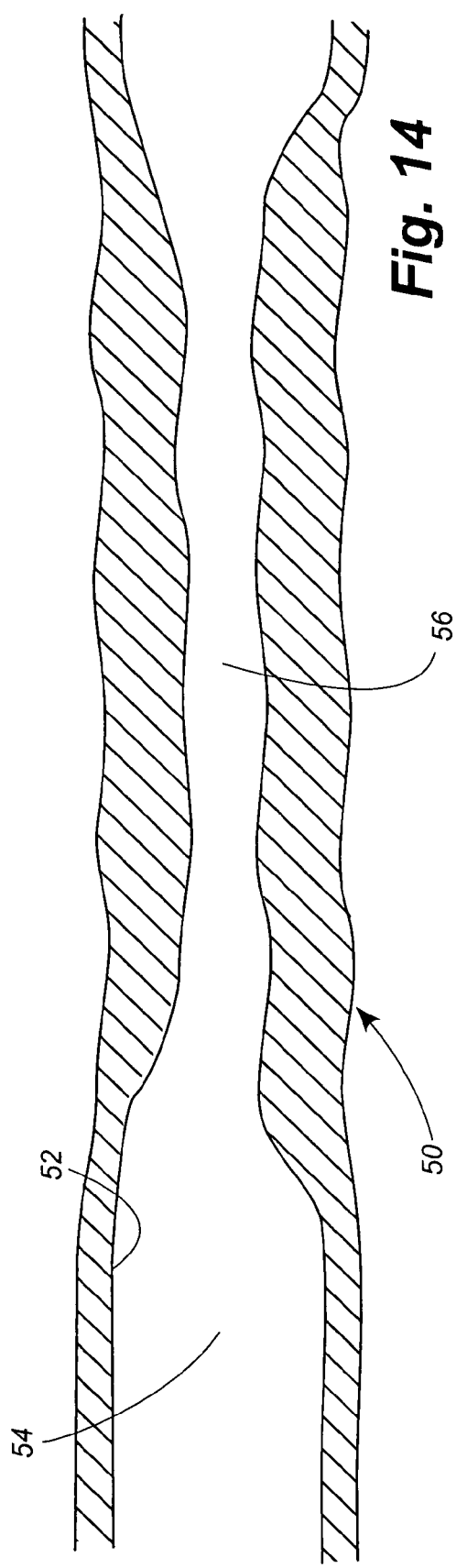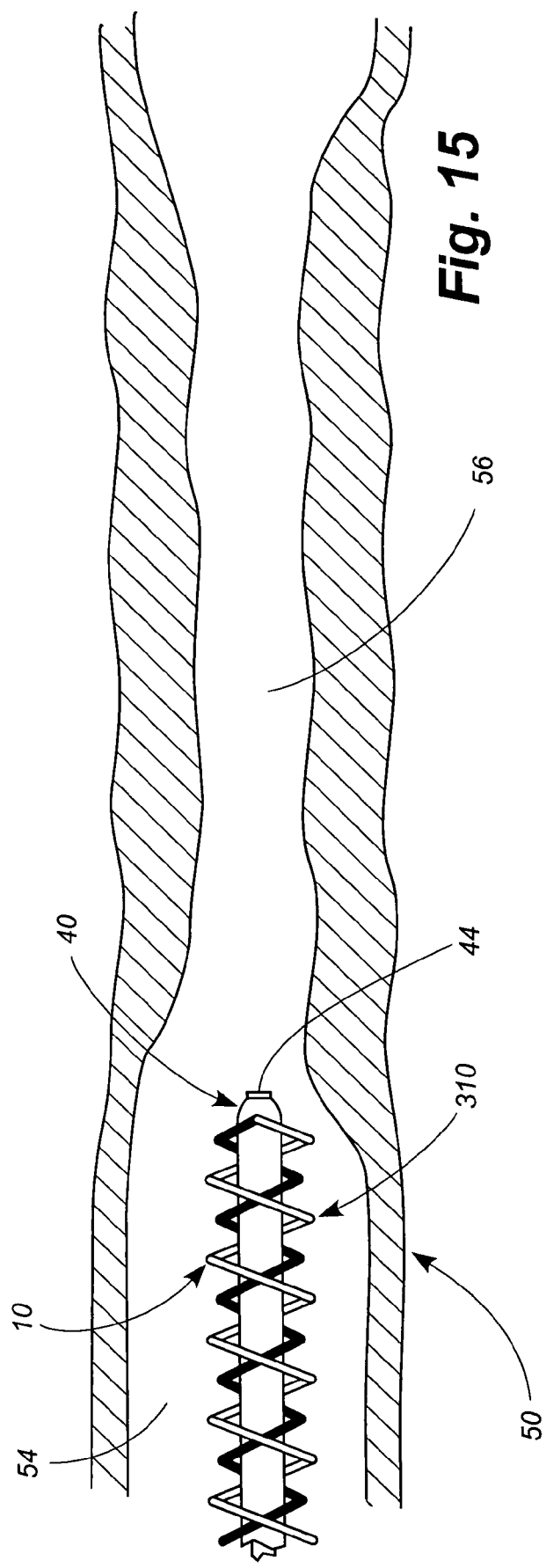

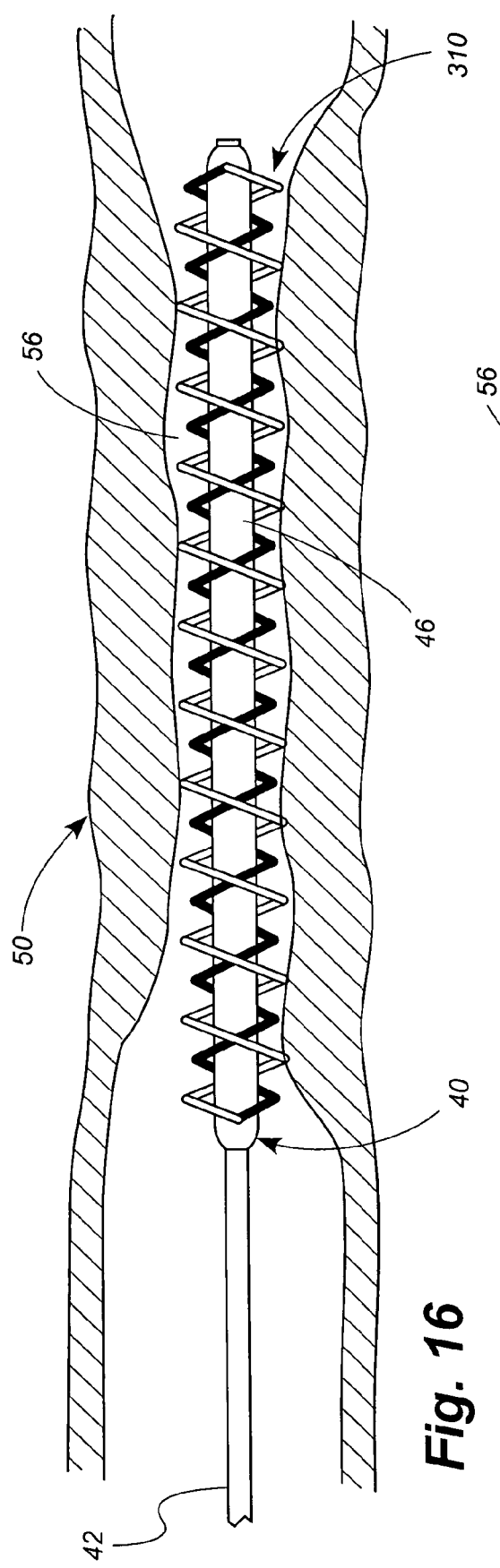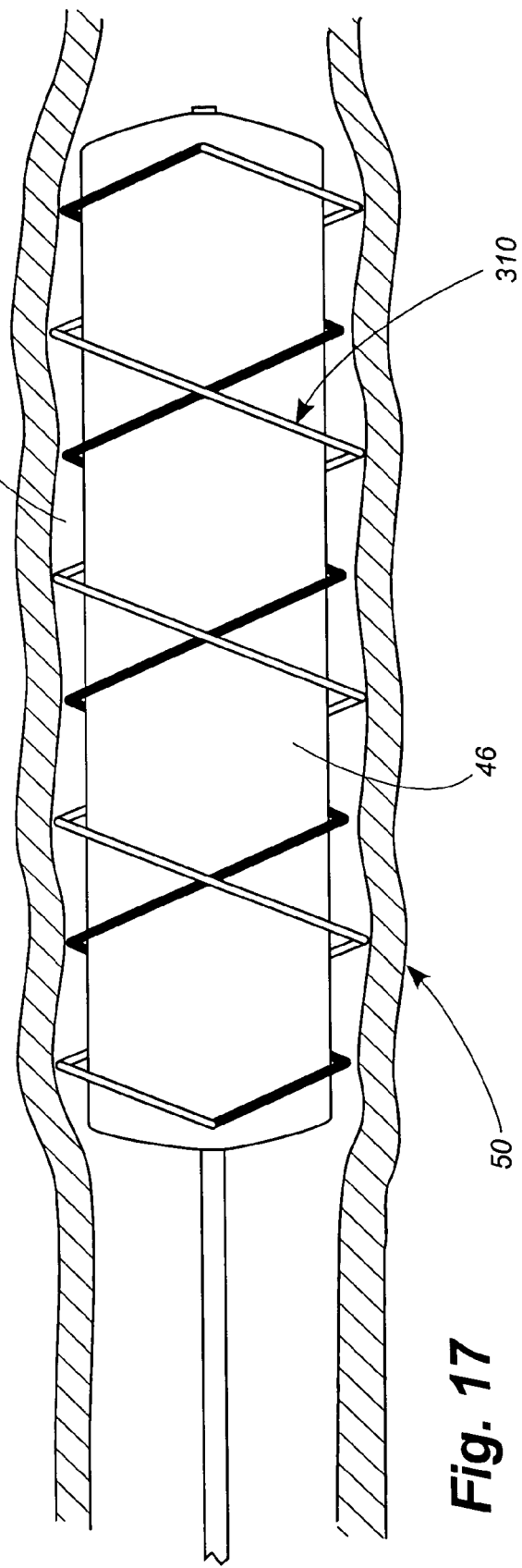

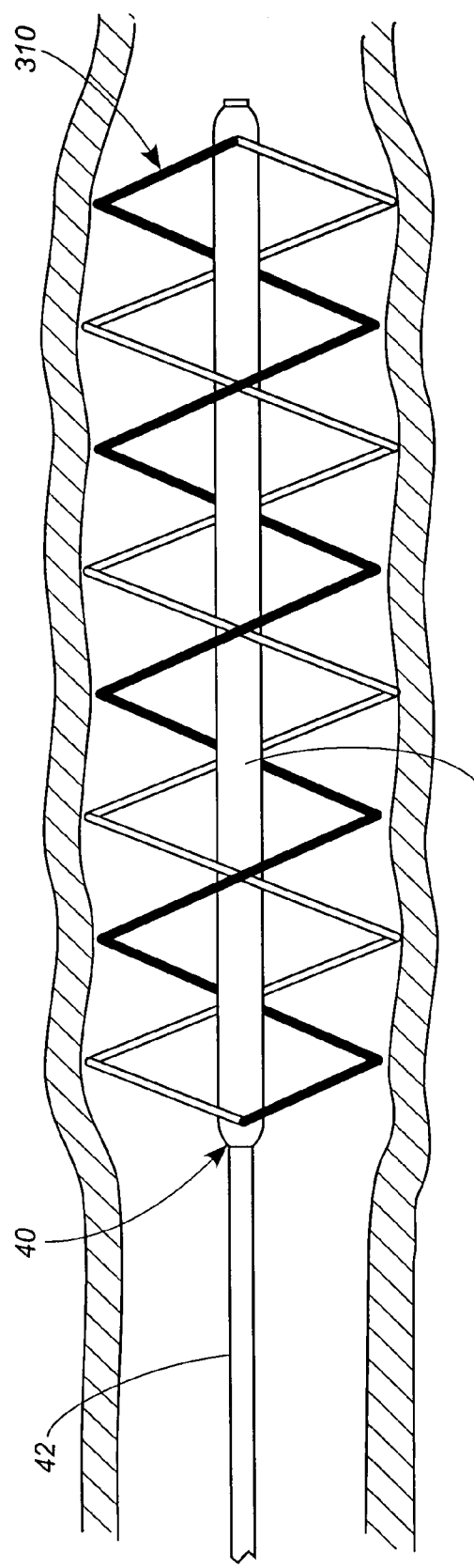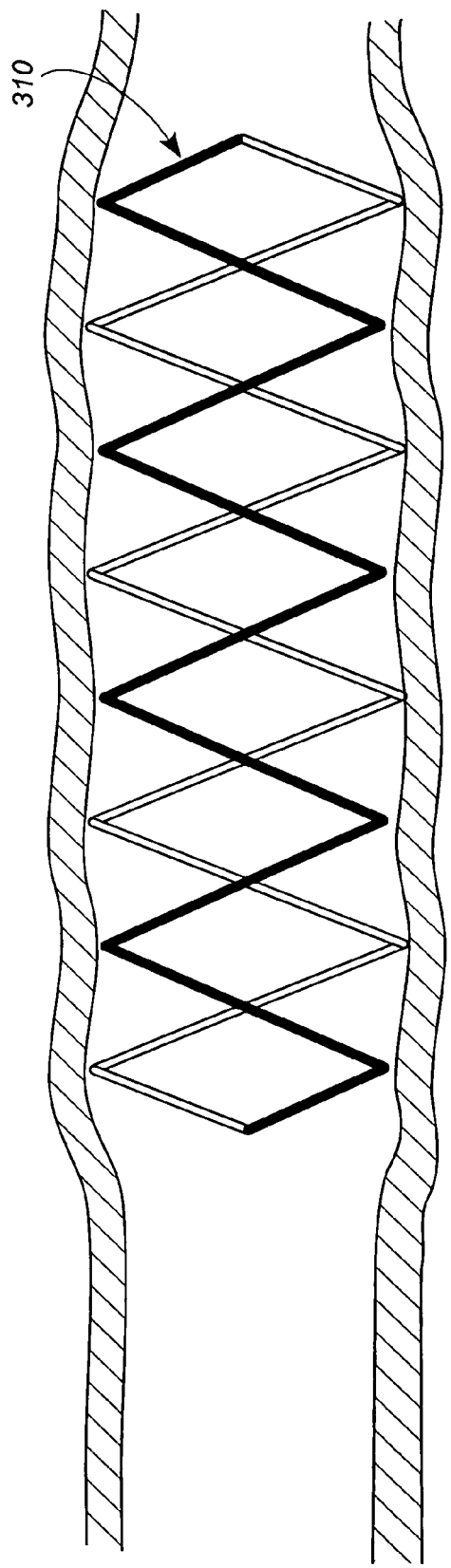
Fig. 18
Fig. 19

HELICAL STENT WITH MICRO-LATCHES

CROSS-REFERENCE TO RELATED APPLICATION

This application claims the priority of U.S. Provisional Patent Application Ser. No. 60/401,379, filed Aug. 6, 2002.

TECHNICAL FIELD

The present invention relates generally to medical devices and relates more specifically to stents for maintaining the patency of a lumen within the body of a patient.

BACKGROUND OF THE INVENTION

Stents are generally tubular devices that are used to support a segment of blood vessel or other anatomical lumen so as to maintain its patency. Stents are useful, for example, in the treatment of atherosclerotic stenoses in blood vessels, maintaining blood perfusion to downstream tissue after opening of a flow restriction.

Various types of stent designs have been developed for treating diseases of blood vessels and other tubular structures inside the body. The currently available stents can be classified into two broad categories: balloon-expandable and self-expanding.

A balloon-expandable stent is collapsed down onto a folded balloon on the end of a balloon dilatation catheter. The stent maintains this collapsed configuration until it is affirmatively expanded. When the stent has been properly positioned within the lumen, the balloon within the stent is inflated to an appropriate size, expanding the stent to the desired diameter. The balloon is then deflated, and the catheter is withdrawn, leaving the expanded stent in place within the lumen. The stent remains in its expanded state because of the plastic deformation that was imparted to its structural elements during expansion.

A balloon-expandable stent has many attractive attributes. Its diameter and outward force to the vessel wall can be adjusted by controlling the inflation pressure of the balloon. Also, after deployment the stent is a semi-rigid structure that can conform to some extent longitudinally, but maintains a rigid scaffolding that prevents vessel collapse in the radial direction.

However, balloon-expandable stents also present certain disadvantages. One such disadvantage is that there is typically some component of elastic recoil after expansion. This elastic recoil usually means that there is a reduction in diameter after the balloon is deflated. The degree of reduction in diameter is related to the material selection, structural design, and degree of inward force from the vessel wall. These factors vary from stent to stent and from situation to situation, presenting a challenge for the practitioner to achieve the desired outcome in repeatable manner.

In contrast to the balloon-expandable stent, a self-expanding stent is formed to assume a pre-determined diameter. The stent is radially compressed and placed on the end of a delivery catheter. Some means, such as a surrounding sheath, must be provided to maintain the stent in its compressed state on the end of the delivery catheter as it is delivered to the target site within a lumen in the body of a patient. When the sheath is retracted, the stent recovers to its pre-determined diameter through a shape memory effect.

This type of stent operates in an entirely elastic mode, so it is possible for this stent to be more flexible than its balloon-expandable counterpart. For this reason, it is possible to create self-expanding stents with more tightly arranged mesh patterns, without resulting in an axially rigid stent. Because of these attributes, self-expanding stents are particularly useful in larger vessels, where superior conformability and vessel wall coverage are relatively more important. It is also the stent of choice whenever there is a concern that the stent could be crushed due to body movement or external pressure, because this type of stent will elastically recover after temporary collapse, whereas a balloon-expandable stent will not.

The disadvantages of self-expanding stents are mainly that the diameter of the stent is not as adjustable as with a balloon-expandable stent. For instance, if the vessel size is too small relative to the stent rest diameter, then a self-expanding stent will exert a radially outward force on the vessel only until the stent reaches its relaxed diameter. If the vessel size is too large for the stent, the stent cannot be adjusted to fit the vessel, and it will not be affixed to the vessel wall.

Balloon-expandable and self-expanding stents are known that employ ratcheting or latching means for retaining the expanded configuration. One purported benefit of stent designs that contain latching elements is the capability for more precise lumen sizing. In the balloon-expandable, latching stent designs, a latch allows radial expansion, but limits post deployment reduction in diameter. In the self-expanding case, a latch can be employed to prevent over-expansion, and provides an upper limit to the chronic outward force on the vessel.

However, a disadvantage of stents with latching mechanisms is that the latches contribute significantly to the bulk of the stent. For this reason known stents with latching mechanisms have exhibited reduced flexibility and larger undeployed profile, i.e., diameter. These characteristics are important because they relate to the ability of the stent to be delivered to the desired target site. The flexibility of the stent relates to how well it will navigate turns in the vessel, and the diameter of the stent determines the minimum diameter in the vessel that can be traversed by the stent as it is being delivered to the target site. Additionally a larger profile stent requires that larger accessory devices be used to introduce the device. The need for larger accessory devices means that the puncture in the vessel wall for introducing the stent needs to be larger as well, leading to longer post-procedure patient recovery times.

Another drawback to known stents with latching mechanisms is that the sizing of the stent is not continuous but rather ratchets in discrete increments. The sizing increment that is available to the user is typically a function of the size and spacing between latches. So fine adjustment of the stent diameter in its expanded state is restricted when compared to non-latching, balloon-expandable stents. This effect becomes more significant as the size of the target vessel becomes smaller, and so the use of the previously proposed ratcheting stents are practical only in larger, non-coronary vessels.

BRIEF DESCRIPTION OF THE DRAWINGS

FIG. 1 is an end view of a coil structure of a helical coil stent according to a disclosed embodiment of the present invention, the coil structure comprising outer and inner coils.

FIG. 2 is a side view of the coil structure of FIG. 1.

FIG. 8 is an end view of a helical coil stent comprising two of the coil structures of FIG. 1.

FIG. 9 is a side view of the helical coil stent of FIG. 8.

FIG. 10 is an end view of a helical coil stent comprising three of the coil structures are FIG. 1.

FIG. 11 is a side view of the helical coil stent of FIG. 10.

FIG. 12 is a side view of an insertion catheter for implanting a first embodiment of a helical coil stent.

FIG. 13 is a side view depicting the radially contracted coil structure of FIG. 3 positioned over an inflatable balloon of the insertion catheter of FIG. 12.

FIG. 14 is a side cutaway view of a partially blocked blood vessel of the human body.

FIG. 15 illustrates the catheter and stent assembly of FIG. 13 being inserted into the partially constricted blood vessel of FIG. 14.

FIG. 16 illustrates the catheter and stent assembly of FIG. 13 with the stent positioned within the stricture of the blood vessel.

FIG. 17 shows the balloon of the insertion catheter inflated to radially expanded the stent within the stricture.

FIG. 18 shows the radially expanded stent with the balloon of the insertion catheter deflated.

FIG. 19 shows the radially expanded stent supporting the blood vessel after the insertion catheter has been withdrawn.

DETAILED DESCRIPTION OF THE DISCLOSED EMBODIMENTS

Figure 3:
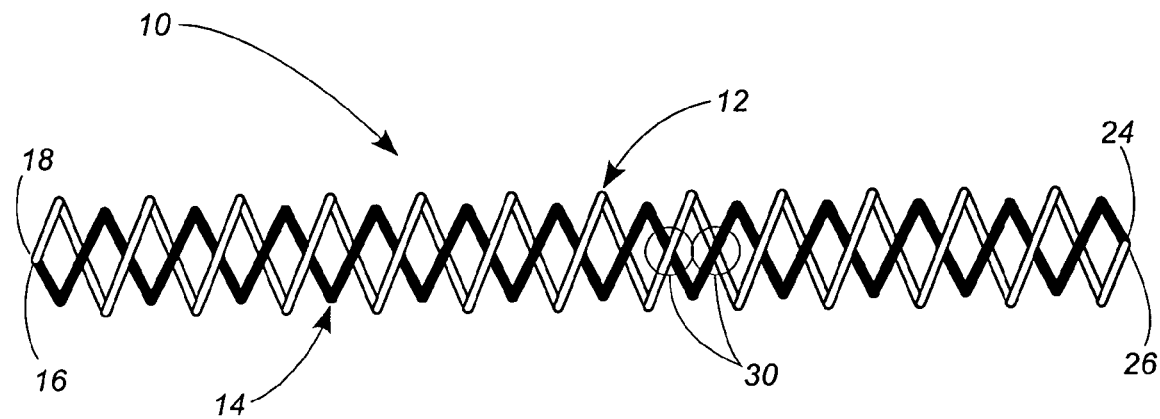
FIG. 3 is a side view of the coil structure of FIG. 1 in a radially contracted configuration.

Referring now to the drawings, in which like numerals indicate like elements throughout the several views, FIGS. 1 and 2 illustrate a coil structure 10. The coil structure 10 can either form a helical coil stent or can be combined with other coil structures 10 to form a stent. The coil structure 10 includes an outer helical coil 12 and an inner helical coil 14 coaxially disposed within the outer coil 12.

In the drawings the outer coils 12 are shown in white, and the inner coils 14 are shown in black. This difference in coloration is not meant to imply a difference in the materials from which the inner and outer coils are fabricated. Rather, the difference is simply to make it easier to distinguish in the drawings between the outer coils and the inner coils.

The outer and inner coils 12, 14 turn in opposite directions. A first end 16 of the outer coil 12 is attached to a first end 18 of the inner coil 14. As can be seen in FIG. 1, from the attachment point, the outer coil 12 turns in a counter-clockwise direction, as indicated by the arrow 20, and the inner coil 14 turns in a clockwise direction, as indicated by the arrow 22. At the opposite end of the coil structure 10, the outer coil 12 terminates at an end 24, and the inner coil 14 terminates at an end 26. The ends 24, 26 of the outer and inner coils 12, 14 are not connected and are free to move relative to one another.

Since the outer and inner coils 12, 14 turn in opposite directions, they crisscross at intersections 30 every 180°. The inner coil 14 is formed to have a normally larger radius than the outer coil 12. Thus the outer surface of the inner coil 14 is firmly imposed against the inner surface of the outer coil 12 at each intersection 30.

Figure 4:
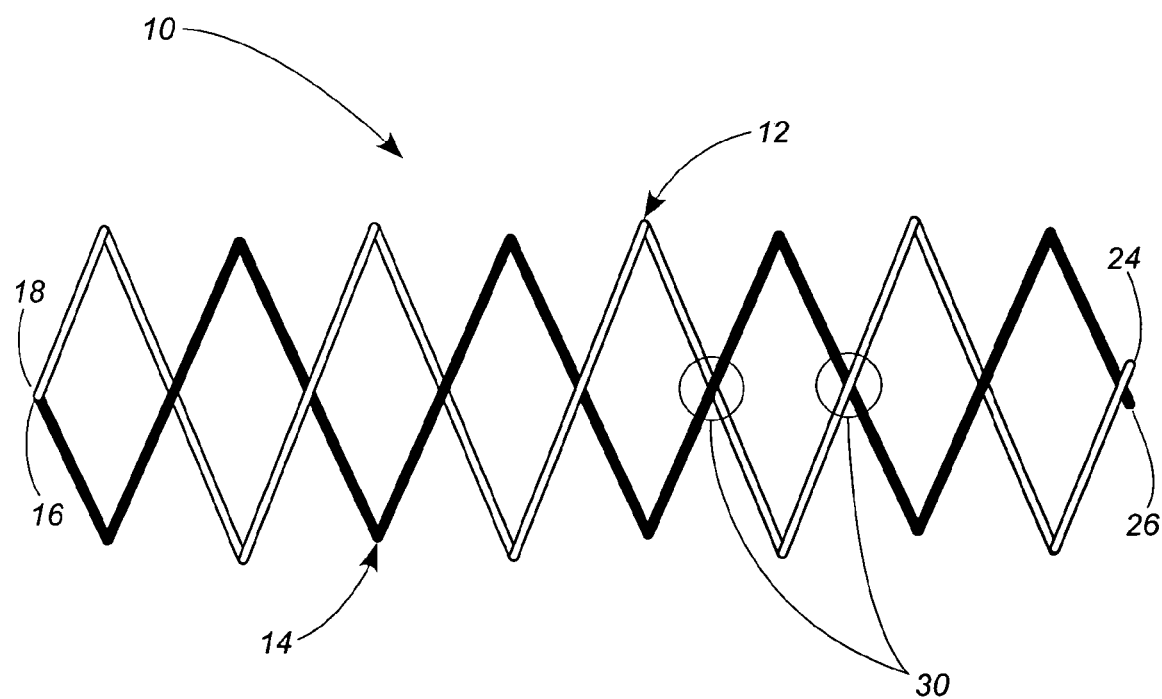
FIG. 4 is a side view of the coil structure of FIG. 3 in a radially expanded configuration.

FIGS. 3 and 4 compare the same coil structure 10 in radially collapsed and radially expanded configurations. When in the radially collapsed configuration of FIG. 3, the coil structure 10 has a relatively small diameter and a relatively large number of turns. In contrast, when the coil structure 10 is radially expanded, its diameter increases, but the total number of turns decreases. The coil structure 10 of FIG. 4 has been expanded to a diameter approximately times the diameter of the coil structure 10 in FIG. 3. However, when the diameter of the coil structure is increased by a factor of 3, the coil structure 10 has only one-third the number of turns. It will also be appreciated that the angle between the outer coil 12 and the inner coil 14 at each intersection 30 remains essentially the same. In essence, the coil structure 10 when radially expanded simply unwinds, resulting in a larger diameter but fewer turns and, consequently, fewer intersections 30.

Because it is necessary for the coil structure 10 to unwind in order to radially expand, the free ends 24, 26 of the outer and inner coils 12, 14 cannot be connected. While connecting the first ends 16, 18 of the outer and inner coils 12, 14 facilitates assembly, it is not essential to the functioning of the device that the first ends the connected. It is possible to have and inner coil 14 coaxially disposed within an outer coil 12 without any common location on the two coils being fixed. It is also possible to have an inner coil 14 disposed within an outer coil 12 without either of the pairs of ends 16, 18 or 24, 26 being angularly coincident. It is further possible to have the inner coil 14 fixed to the outer coil 12 at an intermediate location between the two ends.

Figure 5:
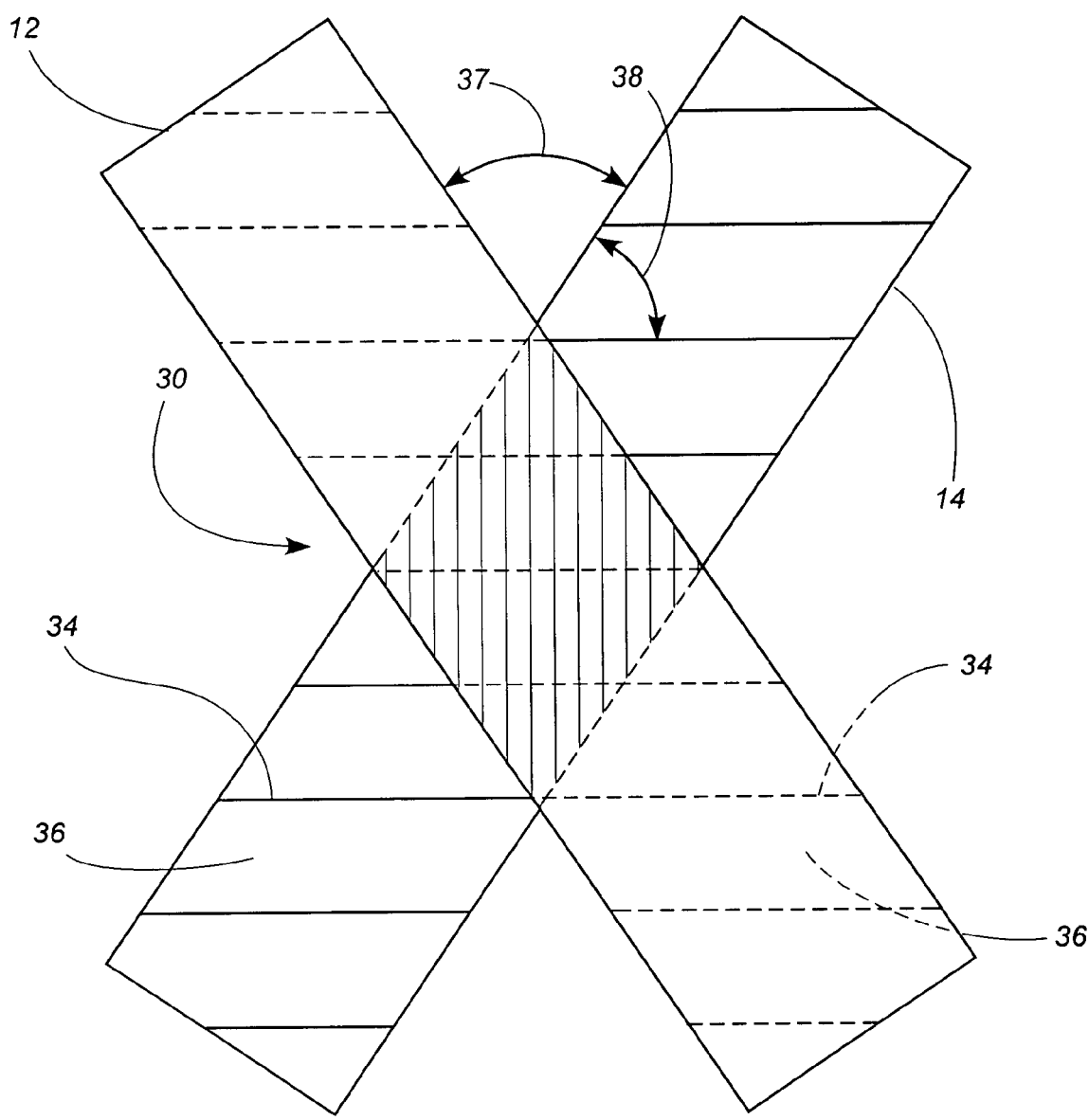
FIG. 5 is a plan view of an intersection of the outer and inner coils of the coil structure of FIG. 1.
Figure 6:
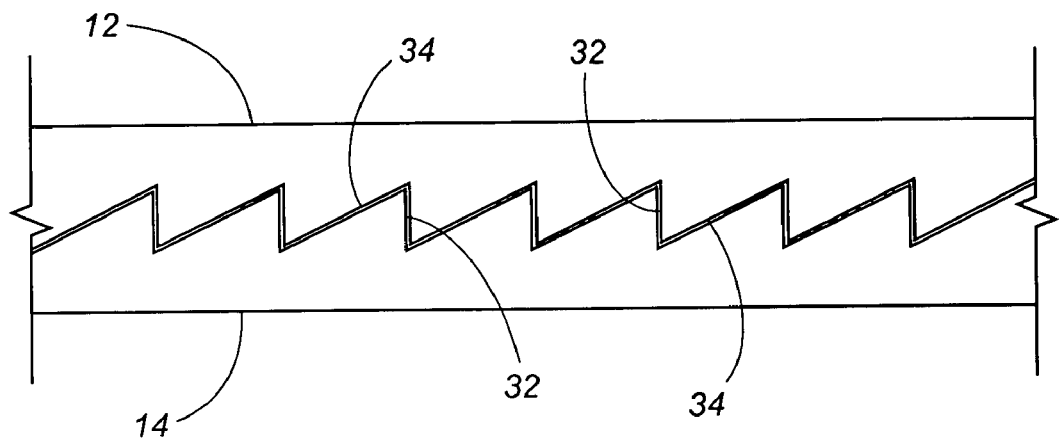
FIG. 6 is a side view of the intersection of FIG. 5.
Figure 7:
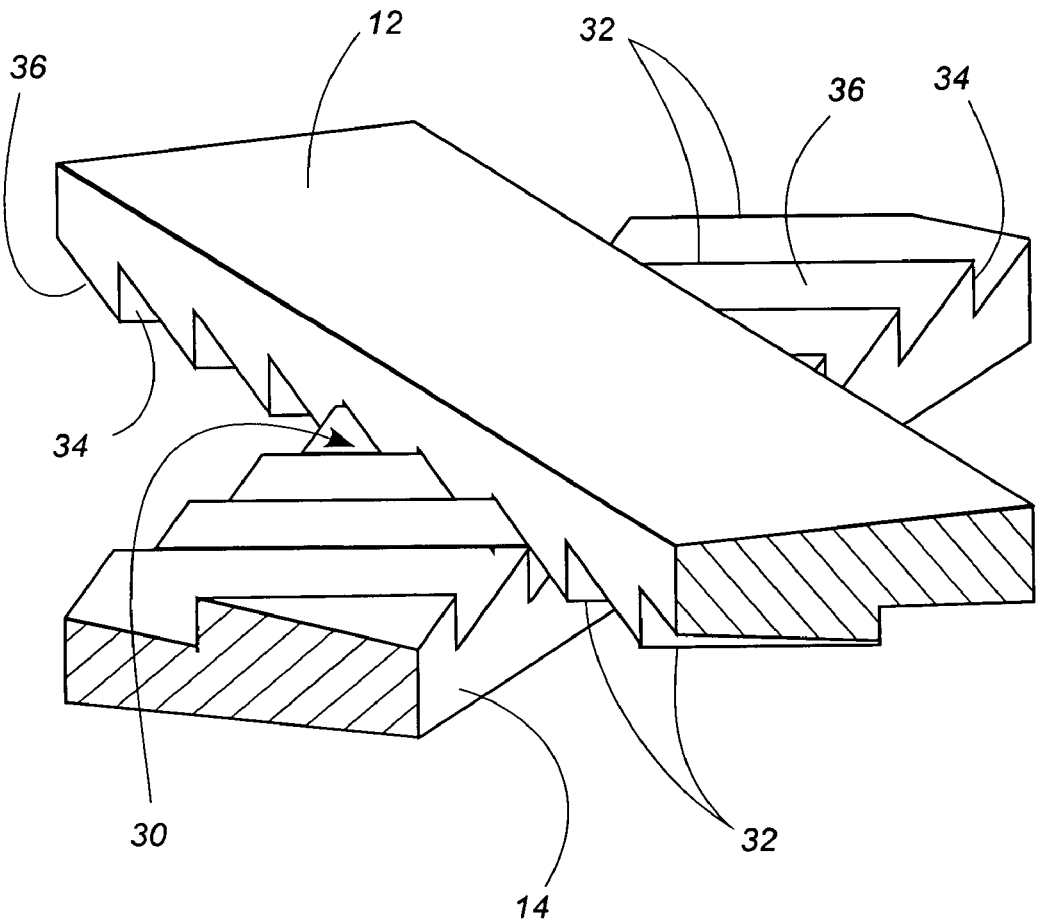
FIG. 7 is a perspective view of the intersection of FIG. 5.

Referring now to FIGS. 5-7, an intersection 30 between the outer and inner coils 12, 14 is shown in expanded view. The inner surface of the outer coil 12 and the outer surface of the inner coil 14 each have mating teeth 32 formed thereon. Each of the teeth 32 includes a vertical face 34 and a sloping leg portion 36. The teeth 32 are angularly offset with respect to perpendicular to the longitudinal axis of the coils 12, 14. Thus even though the outer and inner coils 12, 14 intersect at an angle, the teeth 32 on mutually facing surfaces of the outer and inner coils mesh squarely. In the disclosed embodiment of the helical coil structure 10, the outer and inner coils 12, 14 intersect at an angle 37 of approximately 68°. Thus each coil is angled 34° with respect to vertical. To accommodate this angle, the teeth 32 on the inner and outer surfaces of the outer and inner coils are formed at complementary angles 38 of approximately 56° with respect to the longitudinal edges of the respective coils.

The teeth 32 on the outer and inner coils 12, 14 are configured to permit relative movement between the inner and outer coils as the coil structure 10 expands. However, the teeth 32 engage to prevent relative movement between the outer and inner coils 12, 14 in the opposite direction. The teeth 32 thus have a ratchet effect, permitting the coils 12, 14 to expand but not permitting them to contract.

Referring now to FIGS. 8 and 9, a helical coil stent 110 comprises a pair of coil structures 10A and 10B coaxially intertwined. The first coil structure 10A comprises an outer coil 12A and an inner coil 14A. A first end 16A of the outer coil 12A is attached to a first end 18A of the inner coil 14A, just as in the helical coil structure 10 previously described. From this connection point, the outer coil 12A turns in a counterclockwise direction as shown by the arrow 20A in FIG. 8, while the inner coil 14A turns in a clockwise direction as shown by the arrow 22A. At the opposite end of the coil structure 10A, the outer and inner coils 12A, 14A terminate in free ends 24A, 26A respectively. Similarly, the second coil structure 10B comprises an outer coil 12B and an inner coil 14B. A first end 16B of the outer coil 12B is attached to a first end 18B of the inner coil 14B. From this connection point, the outer coil 12B turns in a counterclockwise direction as shown by the arrow 20B in FIG. 8, while the inner coil 14B turns in a clockwise direction as shown by the arrow 22B. Thus both of the outer coils 12A, 12B turn in the same direction, and both of the inner coils 14A, 14B turn in same direction. The coils 12B, 14B terminate in free ends 24B, 26B.

To achieve even spacing between adjacent coils of the stent 110, the first and second coil structures 10A, 10B are angularly offset by 180°. As shown in FIG. 8, the connected ends 16A, 18A of the outer and inner stents 12A, 14A are located at the twelve o'clock position, and the connected ends 16B, 18B of the outer and inner stents 12B, 14B are located in the six o'clock position. Thus the outer coils 12A, 12B do not touch one another, and the inner coils 14A, 14B do not touch one another. However, each of the outer coils 12A, 12B contact each of the inner coils 14A, 14B. Thus the first outer coil 12A intersects the first inner coil 14A at 180° and at 360°, while the first outer coil intersects the second inner coil 14B at 90° and at 270°. In the drawings, the intersections 30 are labeled by the convention "30xy," where x represents the letter of the outer coil, and y represents the letter of the inner coil. Thus, for example, the intersection 30AB indicates the intersection between the outer coil 12A and the inner coil 14B.

FIGS. 10 and 11 illustrate a helical coil stent 210 comprising three coil structures 10A, 10B, and 10C coaxially intertwined. The first coil structure 10A comprises an outer coil 12A and an inner coil 14A. A first end 16A of the outer coil 12A is attached to a first end 18A of the inner coil 14A. From this connection point, the outer coil 12A turns in a counterclockwise direction as shown by the arrow 20A in FIG. 10, while the inner coil 14A turns in a clockwise direction as shown by the arrow 22A. At the opposite end of the coil structure 10A, the outer and inner coils 12A, 14A terminate in free ends 24A, 26A respectively. Similarly, the second coil structure 10B comprises an outer coil 12B and an inner coil 14B. A first end 16B of the outer coil 12B is attached to a first end 18B of the inner coil 14B. From this connection point, the outer coil 12B turns in a counterclockwise direction as shown by the arrow 20B in FIG. 10, and the inner coil 14B turns in a clockwise direction as shown by the arrow 22B. The coils 12B, 14B terminate in free ends 24B, 26B. Finally, the third coil structure 10C comprises an outer coil 12C and an inner coil 14C. A first end 16C of the outer coil 12C is attached to a first end 18C of the inner coil 14C. From this connection point, the outer coil 12C turns in a counterclockwise direction as shown by the arrow 20C in FIG. 10, and the inner coil 14C turns in a clockwise direction as shown by the arrow 22C. The coils 12C, 14C terminate in free ends 24C, 26C.

To achieve even spacing between adjacent coils of the stent 210, the three coil structures 10A, 10B, 10C are angularly offset by 120°. As shown in FIG. 10, the connected ends 16A, 18A of the outer and inner coils 12A, 14A are located at the ten o'clock position, the connected ends 16B, 18B of the outer and inner coils 12B, 14B are located in the two o'clock position, and the connected ends 16C, 18C of the outer and inner coils 12C, 14C are located at the six o'clock position. (Note that in FIG. 11, the connected ends 16A, 18A of the outer and inner coils 12A, 14A are hidden behind the connected ends 16B, 18B of the outer and inner coils 12B, 14B.) Thus the outer coils 12A-C do not touch one another, and the inner coils 14A-C do not touch one another. However, each of the outer coils 12A-12C contacts each of the inner coils 14A-C. Thus the first outer coil 12A intersects the first inner coil 14A at 180° and at 360°, the first outer coil intersects the second inner coil 14B at 60° and at 240°, and the first outer coil intersects the third inner coil 14C at 120° and at 300°. In FIG. 11 the intersections 30 are labeled by the convention "30xy," where x represents the letter of the outer coil, and y represents the letter of the inner coil. Thus, for example, the intersection 30AC indicates the intersection between the outer coil 12A and the inner coil 14C.

From a comparison of the embodiment of FIGS. 1 and 2 to the embodiment of FIGS. 8 and 9 and the embodiment of FIGS. 10 and 11, the following generalizations can be made. First, to achieve equal spacing between adjacent coils where multiple coil structures 10 are involved, the angular offset of the coil structures is equal to 360° divided by the number of coil structures. Thus a stent with two coil structures 10 requires that the coil structures be offset by 180°, a stent with three coil structures requires the coil structures to be offset by 120°, and so on. Second, the number of intersections or contact points 30 between the outer coils 12 and the inner coils 14 is equal to two times the number of outer coils times the number of inner coils. Thus for each 360° of coil, a stent with one outer and one inner coil will have two intersections (2×1×1), a stent with two outer and two inner coils will have eight intersections (2×2×2), and a stent with three outer and three inner coils will have eighteen intersections (2×3×3). Since teeth on mutually facing portions of the outer and inner coils engage at each intersection, the number of intersections directly affects the radial strength of the stent. According to a preferred embodiment, a stent is comprised of six coil structures 10. Thus the coil structures are offset by 60°, and the resulting stent will have seventy-two intersections between outer and inner coils for each complete turn of the coils.

While the stents 110, 210 as disclosed both have equal spacing between adjacent coils, such equal spacing is not essential to the operation of the invention. Further, while the stents 110, 210 both have an equal number of outer and inner coils 12, 14, it will be understood that it is not essential to the invention to have the same number of outer coils as inner coils.

Balloon Expandable Stent

FIGS. 12-19 illustrate a balloon-expandable stent 310 (FIG. 13). For simplicity of description, the stent 310 is comprised of a single coil structure 10. However, it will be understood that a typical balloon-expandable stent will most often be comprised of a plurality of coil structures 10 coaxially intertwined.

The stent 310 is formed with the coil structure 10 in a normally compressed state so as to have a normal external diameter smaller than the internal diameter of the lumen within which the stent is intended to be placed. As an example, a balloon expandable stent 310 for use within a blood vessel may have a normal external diameter of approximately 5 mm.

FIG. 12 shows an insertion catheter 40 having an elongated, flexible shaft 42. The length of the shaft 42 will vary, depending upon its intended use, but it will always be a sufficient length to extend from a target site within the body of a patient to a location external of the patient so that the physician can manipulate the insertion catheter 40. Adjacent the forward end 44 of the insertion catheter 40, an inflatable balloon 46 overlies the catheter shaft 42. The balloon 46 has length approximating, and preferably slightly longer than, the length of the stent 310. An inflation medium such as saline solution can be infused through an inflation lumen in the catheter shaft 42 and into the interior of the balloon 46 in the conventional manner well-known to those skilled in the art.

In FIG. 13 the stent 310 has been positioned over the balloon 46 of the insertion catheter 40. Preferably the inner diameter of the stent 310 closely matches the outer diameter of the balloon 46 in its uninflated state. If necessary, the balloon 46 may be slightly inflated to hold the stent 310 on the forward end of the insertion catheter 40 during the implantation procedure.

FIG. 14 is a cross-sectional view of a blood vessel 50 of a human patient. Interior walls 52 of the blood vessel 50 define a lumen 54. The blood vessel 50 has a constriction 56 which is in need of treatment.

The forward end 44 of the insertion catheter 40 with stent 310 mounted thereon is inserted into the lumen 54 of the blood vessel 50, as illustrated in FIG. 15. The forward end 44 of the insertion catheter 40 is advanced until the stent 310 resides within the stricture 56, as shown in FIG. 16.

When the position of the stent 310 has been confirmed by fluoroscopy or other suitable visualization technology, the balloon 46 is inflated, as shown in FIG. 17. As the balloon 46 inflates, the stent 310 is radially expanded, expanding the stricture 56. When the stent 310 has reached the desired diameter, the balloon 46 is deflated, as shown in FIG. 18. The ratchet teeth 32 on the coils 12, 14 of the coil structure 10 engage one another at each intersection 30 to maintain the stent 310 in its expanded arrangement and to prevent it from contracting to its normal configuration. The insertion catheter 40 is then withdrawn from the patient's body, leaving the stent 310 in position, as shown in FIG. 19.

Self-Expanding Stent

FIGS. 20-23 illustrate a self-expanding stent 410. For clarity of description, the stent 410 consists of only a single coil structure 10, but it will be understood that a typical self-expanding stent will be comprised of a plurality of coil structures. The stent 410 is formed with the coil structures in an expanded state so as to have a normal external diameter slightly larger than the internal diameter of the lumen within which the stent is intended to be placed.

Figure 20:
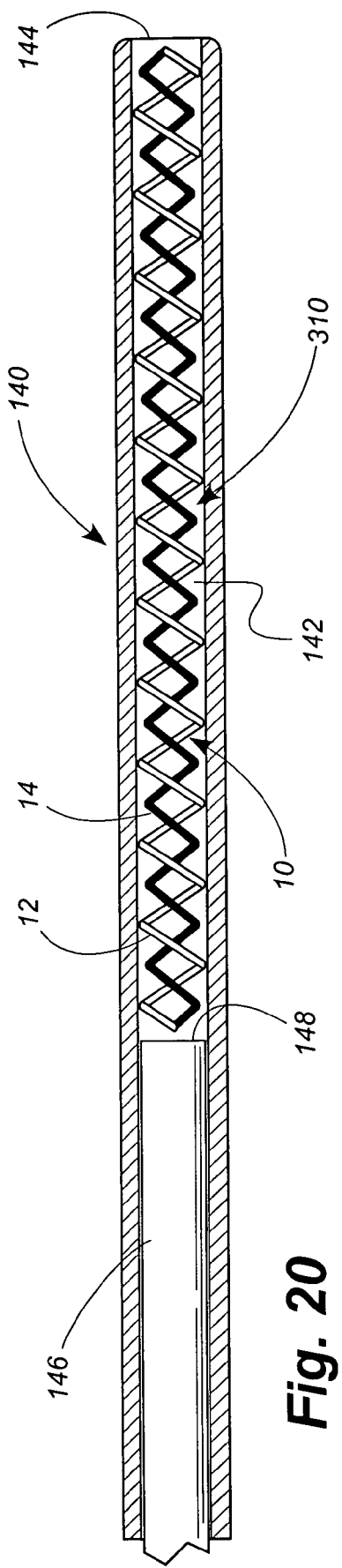
FIG. 20 illustrates a normally-expanded stent radially compressed and positioned within the forward end of a sheath.

To position the self-expanding stent 410 within a lumen, a sheath 140 is used. As shown in FIG. 20, the sheath 140 has a lumen 142 and an outer diameter at its forward end 144 which is smaller than the inner diameter of the lumen within which the stent 410 is to be positioned. The stent 410 is radially compressed to fit within the forward end 144 of the sheath 140. A push catheter 146 has an outer diameter closely approximating the inner diameter of the sheath 140. The forward end 148 of the push catheter 146 is inserted into the rearward end of the sheath 140 and advanced until it abuts the rearward end of the stent 410.

Figure 21:
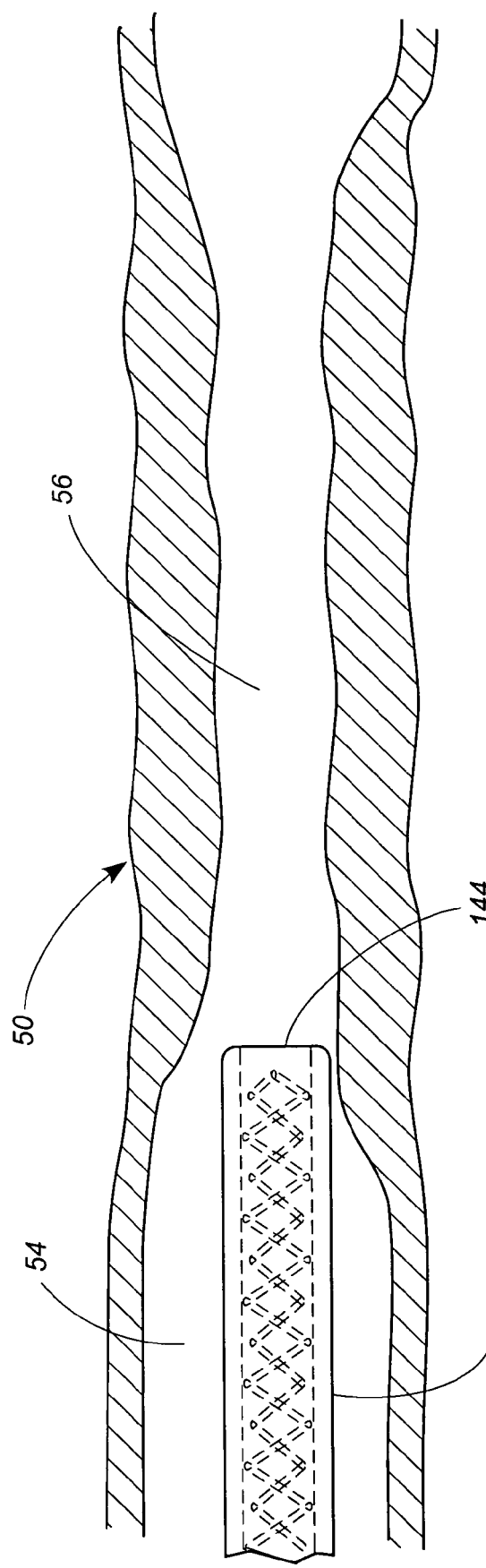
FIG. 21 depicts the sheath and stent of FIG. 20 being inserted into a partially constricted blood vessel.
Figure 22:
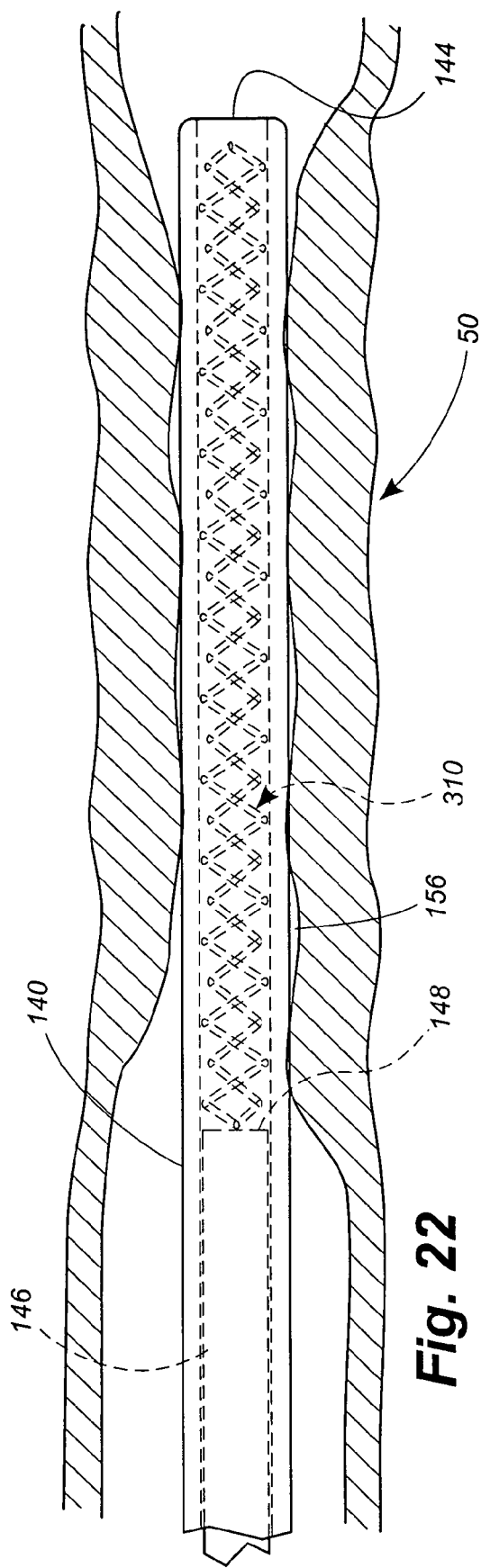
FIG. 22 depicts the sheath and stent of FIG. 20 positioned so that the stent is located within the stricture of the blood vessel.
Figure 23:
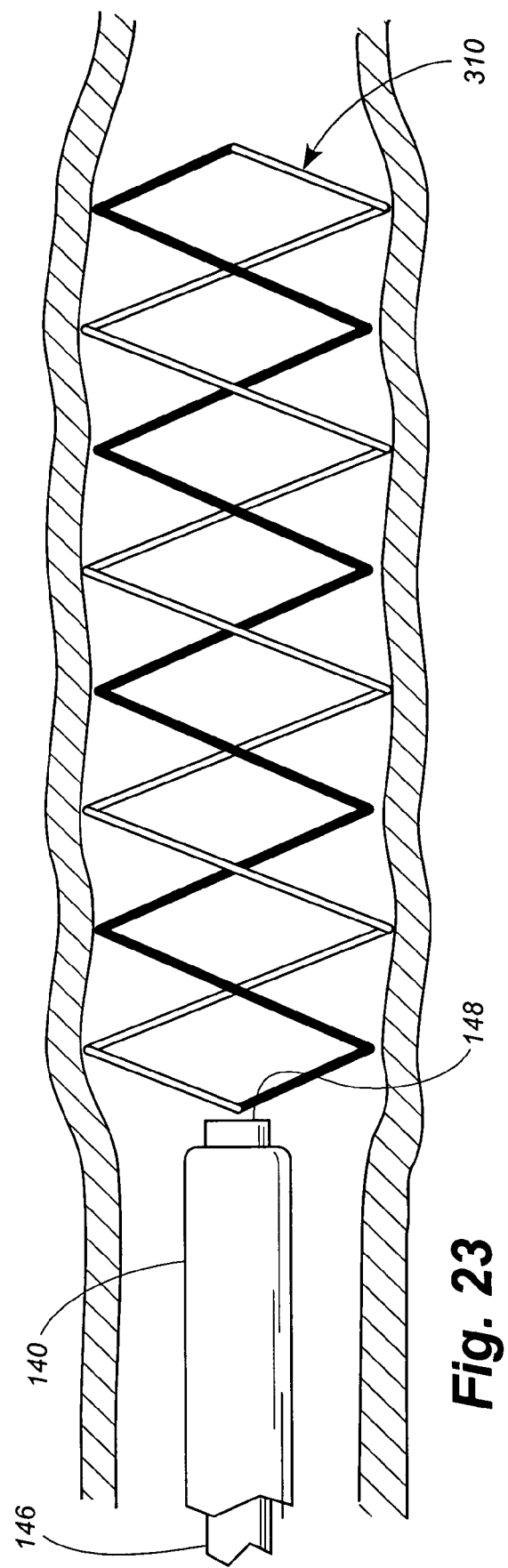
FIG. 23 shows the sheath being retracted to expose the stent, permitting the stent to return to its normally radially expanded configuration.

The forward end of the sheath 140 is inserted into the lumen of a patient and advanced to the target site in a conventional manner, as shown in FIG. 21. When proper location of the stent 410 has been confirmed by fluoroscopy or other suitable visualization technology, the push catheter 146 is held steady, as shown in FIG. 22, as the sheath 140 is withdrawn. Once the stent 410 is free from the confines of the sheath 140, the stent will radially expand to assume its normal configuration. That is, the stent will expand to a diameter which places radially outward pressure against the wall of the stricture. The teeth of the coil structure engage at each intersection 30 to prevent the stent 410 from being radially compressed by the walls of the lumen.

Interwoven Coils

Figure 24:
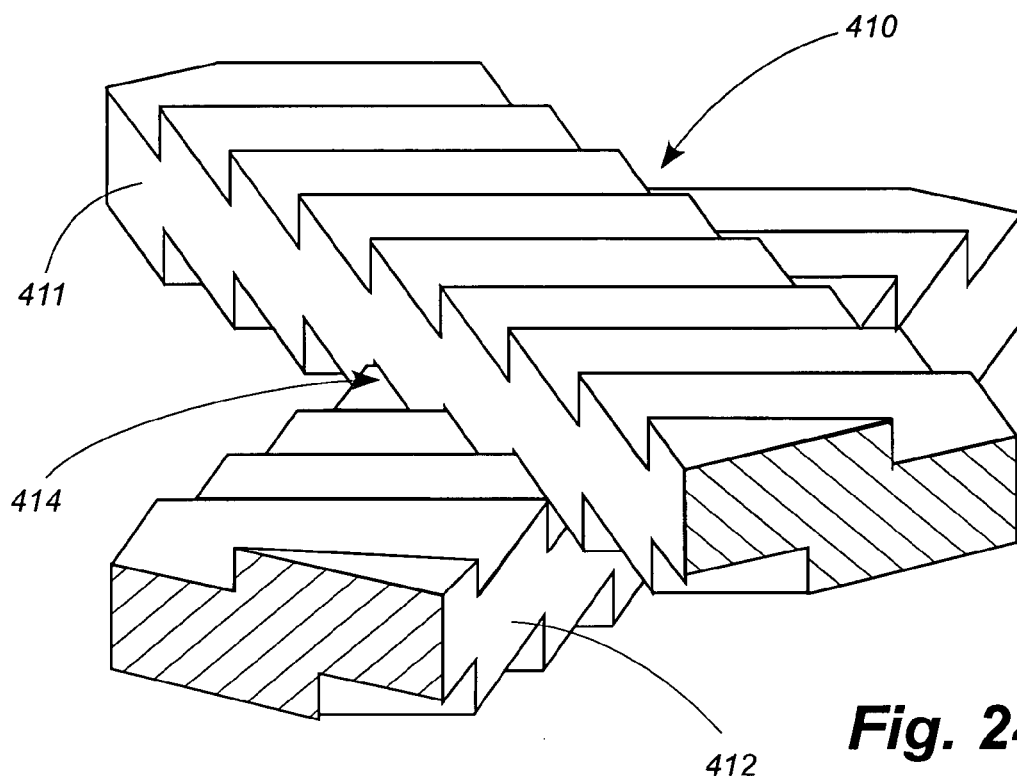
FIG. 24 is a perspective view of an alternate embodiment, showing a first coil passing over a second coil.
Figure 25:
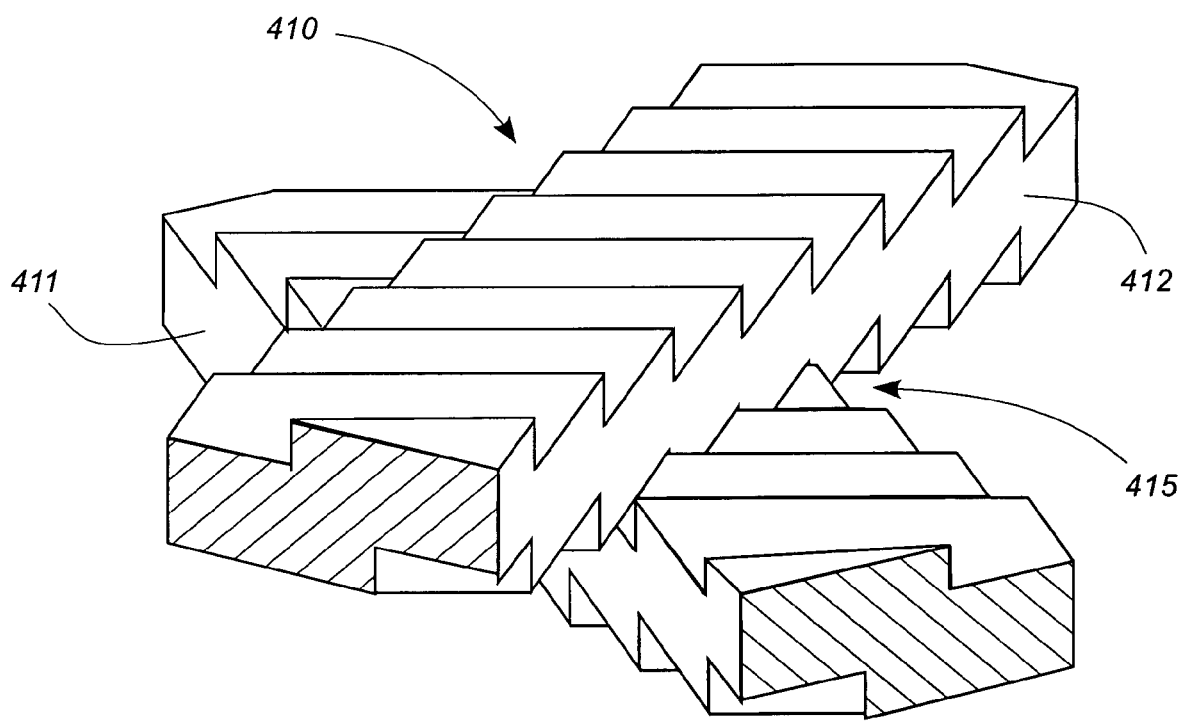
FIG. 25 is a perspective view of the alternate embodiment of FIG. 24, showing the second coil passing over the first coil.

The coil structure 10 previously described relies upon the radial outward pressure exerted by the inner coil to maintain contact between the inner and outer coils 11, 12 sufficient to maintain the teeth 15, 16, in engagement. FIGS. 24 and 25 depict an alternate coil structure 410 which employs a different arrangement to maintain engagement between the two coils 411, 412. Rather than having one coil disposed entirely within another coil, the coils 411, 412 of the coil structure 410 weave over and under one another. Thus at the first contact point 414, the first coil 411 passes over the second coil 412, and at the second contact point 415 the second coil 412 passes over the first coil 411.

Because the outer surface of the first coil 411 contacts the inner surface of the second coil 412 at the first contact point 414 and the outer surface of the second coil 412 contacts the inner surface of the first coil 411 at the second contact point 415, both coils 411, 412 must have teeth formed on both of their inner and outer surfaces.

Manufacture

The stent can be constructed using any methods available to those skilled in the art. However, specialized MEMS-based methods are required in order to form the latching features on the appropriate scale. Some examples of the techniques that may be utilized are surface micro machining, photo lithography, electroplating, sacrificial molding, vacuum molding, and spin coating. The helical components with latching features may be built up on a planar surface as a film of the desired thickness and then separated into strands of the desired width. Alternately, the components can be created as strands with the final thickness and width determined at the initial stage.

Figure 26:
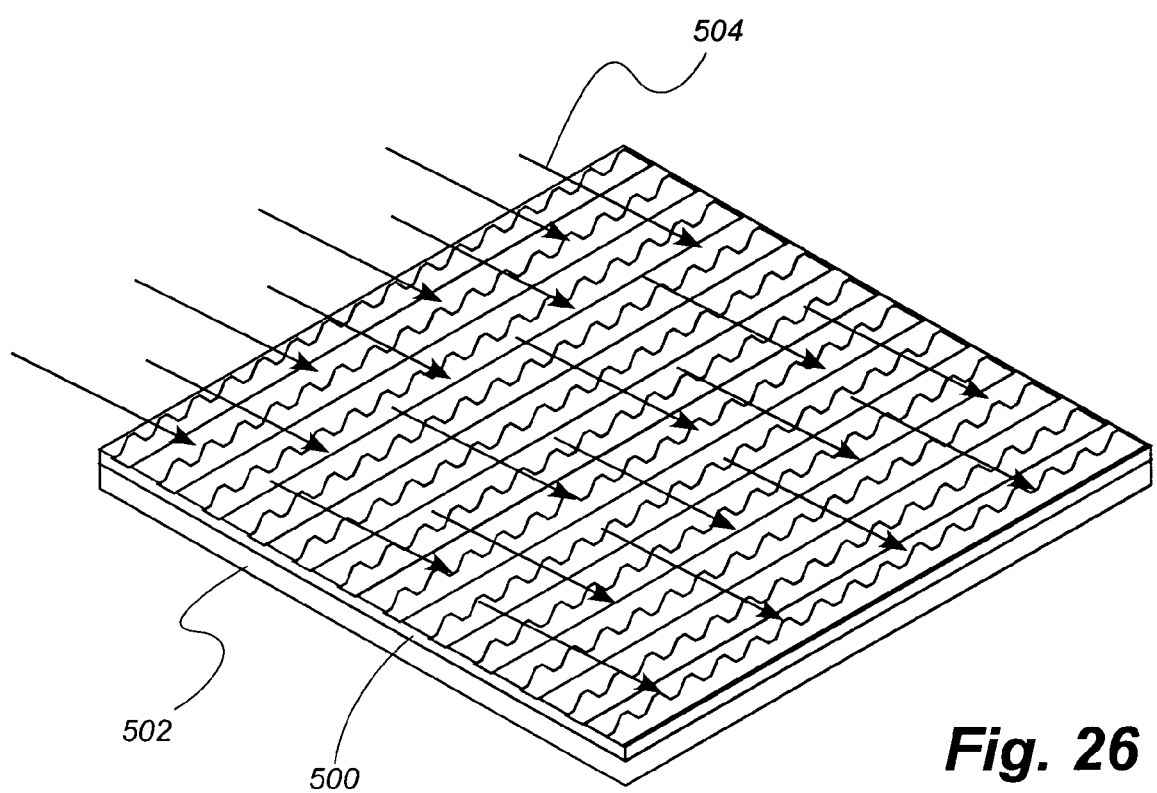
FIG. 26 shows a first step in a disclosed process for manufacturing the stents of the preceding figures.
Figure 27:
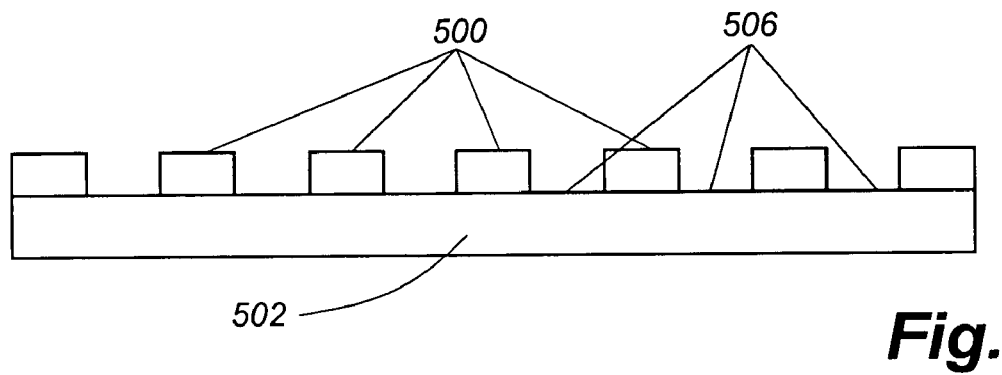
FIG. 27 illustrates a second step in the disclosed manufacturing process.
Figure 28:
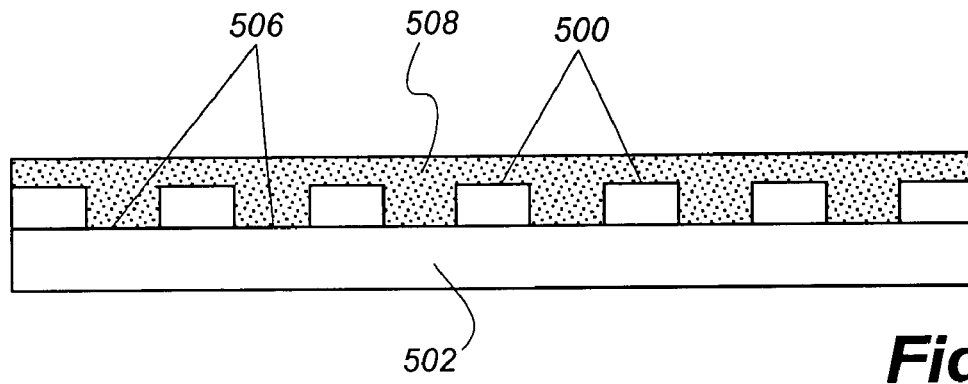
FIG. 28 illustrates a third step in the disclosed manufacturing process.
Figure 29:
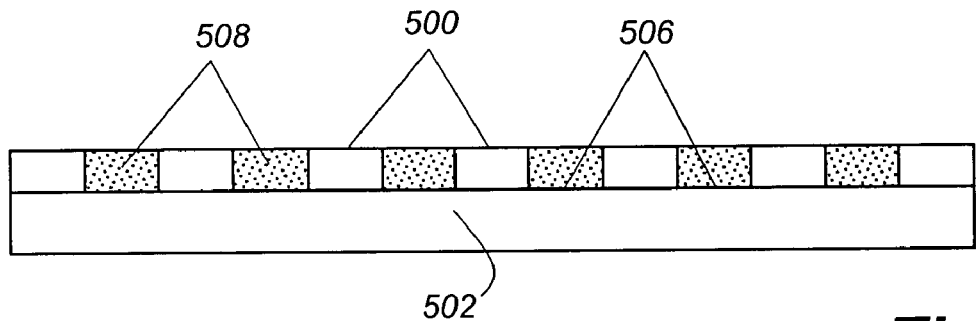
FIG. 29 illustrates a fourth step in the disclosed manufacturing process.
Figure 30:
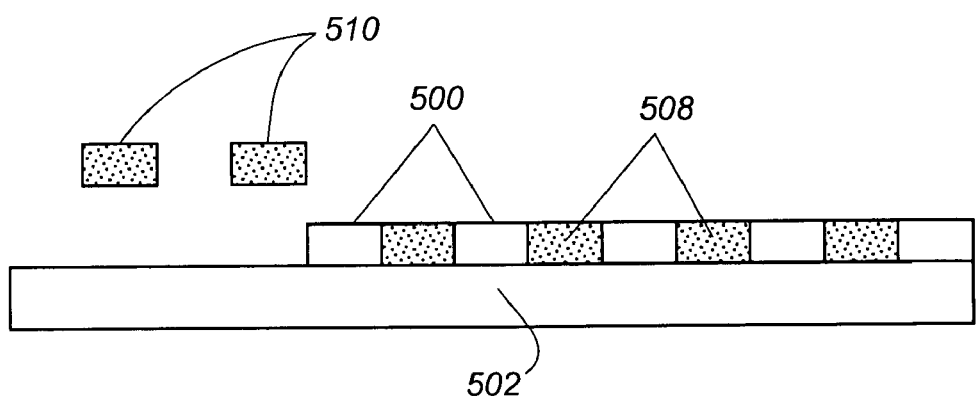
FIG. 30 illustrates a fifth step in the disclosed manufacturing process.

An example of the former manufacturing method will be described only generally, as the manufacturing techniques involved are well known to those skilled in the art. Referring first to FIG. 26, a photoetch material 500 is applied to a substrate 502. The photoetch material 500 is then exposed to a collimated light source, indicated by arrows 504, inclined at 58° with respect to vertical. The purpose of inclining the collimated light source is to create an angled surface for ultimately forming the teeth 32 (FIGS. 5-7), which are angled 58° with respect to the longitudinal edges of the respective coils. The photoetch material 500 is then developed, etching away material to form a series of parallel channels 506, as shown in FIG. 27, with angled teeth (not visible in FIG. 27) protruding from one wall. As shown in FIG. 28, a film 508 of material, such as a biodegradable polymer, is then placed on top of the photoetched material 500 and pressed down to pack the material into the channels 506. The film 508 of biodegradable material is then mechanically abraded down to the top of the photoetch material 500, leaving only the biodegradable material in the individual channels 506. These strands 510 of biodegradable material 508 with teeth formed on one face are then individually separated from the photoetch material 500. The resulting strands 510 are then processed as follows.

The inner strands are formed into a helical coil with the desired pitch and diameter and with the latching elements facing outwards. The outer strands are counter wound around the inner helical coil in the opposite rotational direction, with their latching features facing inwards.

These coil components are constrained in the crimped state, using a retaining tube or some other means, and their internal stresses are released through annealing or some other means. After this treatment, the coils will be in their low energy state as a crimped stent.

The finished stent can be loaded onto a folded delivery balloon, with the assistance of a retaining tube. It may be fixated to the balloon using any means available to those skilled in the art.

Alternately, if the stent is made from shape memory material, so that it is self expanding, the stent will be constrained into a loading tube and loaded into a containing delivery catheter.

Additional radial strength may be generated in the expanded structure by setting the material crystalline structure, once deployed in the expanded state. This could only be practical or necessary in the case of a polymeric stent material. The effect would be that the low energy or rest state of the structure becomes the expanded configuration, improving the strength of the structure. In practice, this treatment can be achieved by any number of means that generate energy in the stent material that would result in the expanded configuration becoming the new rest state.

The disclosed embodiments exhibit a number of advantages over known stents. Microscopic latching features are incorporated into all of the structural components, resulting in a multitude of parts that can slide relative to one another only in the direction that results in expansion of the structure. Sliding motion in the opposite direction, resulting in collapse of the structure, is restricted by the latching features. These latching features have a height, slope angles, void dimensions, spacing intervals, and separation distance parameters, all of which affect the interlocking and movement characteristics of the components.

As can now be appreciated, the radially expandable, ratcheting stents of the disclosed embodiments offer a number of advantages as compared to prior art stents with latch mechanisms. First, the disclosed stents provide a virtually continuous increment of expansion, thereby permitting fine adjustments of the stent diameter. The spacing between adjacent teeth of the latching mechanism is on the micron scale, so that the size increment between locking states is negligible.

Second, the latching mechanism of the disclosed stent minimizes performance degradation. The latching elements themselves do not add substantial bulk to the stent. For this reason, performance comparable or superior to non-latching stents is achievable with a stent design that incorporates the micro-latching features.

Third, the structure of the disclosed stent is inherently stronger than standard balloon expandable or self expanding stents, through the use of latching elements. Applied in the appropriate manner, stent latching mechanisms can also improve the inherent strength of the individual structural elements. This should enable the designer to reduce the stent material stiffness and achieve the equivalent radial strength. This capability could also allow the designer to maintain an equivalent dimensional scale as is currently the standard for non-latching balloon expandable stents, but use softer materials, such as biodegradable polymers in place of metals.

The stent can be made from any material that is suitable for use as a medical implant. In the preferred embodiment the stent will serve only a temporary function as a medicated splint. The desired function of the stent will be to dilate the vessel and to promote and guide the healing process after dilation. After the healing has completed, its function has passed and it will dissolve away into the tissue.

This described effect can be achieved by constructing the stent using a biodegradeable polymer that is embedded or coated with a pharmacological agent that prevents restenosis. Constructed in this manner, the stent will provide scaffolding to the vessel treatment site long enough to guide the healing response around its structural components. During this time, the stent will elute pharmacological agents that will prevent overgrowth of the healing response, or 'restenosis' of the vessel. After the approximate time that the healing process has completed, the stent will cease to function as a structural component, gradually degrading into the tissue.

Finally, it will be understood that the preferred embodiment has been disclosed by way of example, and that other modifications may occur to those skilled in the art without departing from the scope and spirit of the appended claims.

What is claimed is:

1. A stent for maintaining patency of a lumen, comprising: a first helical coil turning in a first direction; a second helical coil disposed within said first helical coil and turning in a second direction opposite said first direction; said first helical coil having teeth formed on its interior surface; and said second helical coil having teeth formed on its outer surface and configured to engage said teeth on said interior surface of said first helical coil.

2. The stent of claim 1, wherein said teeth on said first and second helical coils are configured to permit said stent to uncoil freely to a larger diameter but, once having reached a larger diameter, to prevent said stent from returning to a smaller diameter.

3. The stent of claim 1, wherein said second helical coil further has teeth formed on its interior surface, and wherein said stent further comprises a third helical coil disposed within said second helical coil, said third helical coil turning in the same direction as said first helical coil, and said third helical coil having teeth formed on its outer surface and configured to engage said teeth on said interior surface of said second helical coil.

4. The stent of claim 1, wherein said first and second coils are comprised of a shape memory material such that said coils naturally uncoil to a larger diameter unless constrained by an outside force.

5. A stent for use in a body passageway comprising a body portion, said body portion including a coil system, said coil system including a first coil turning in a first direction and a second coil turning in a second direction opposite said first direction, said first coil including a plurality of teeth, said second coil including a plurality of teeth, at least one of said teeth on said first coil designed to engage at least one of said teeth on said second coil.

6. The stent as defined in claim 5, wherein said first coil is a helical coil and said second coil is a helical coil.

7. The stent as defined in claim 5, wherein said body portion is substantially formed of said coil system.

8. The stent as defined in claim 6, wherein said body portion is substantially formed of said coil system.

9. The stent as defined in claim 5, wherein said second coil is coaxially disposed within said first coil.

10. The stent as defined in claim 6, wherein said second coil is coaxially disposed within said first coil.

11. The stent as defined in claim 8, wherein said second coil is coaxially disposed within said first coil.

12. The stent as defined in claim 9, wherein said second coil is designed to be firmly engage against an inner surface of said first coil.

13. The stent as defined in claim 11, wherein said second coil is designed to be firmly engage against an inner surface of said first coil.

14. The stent as defined in claim 5, wherein said second coil is intertwined with said first coil.

15. The stent as defined in claim 6, wherein said second coil is intertwined with said first coil.

16. The stent as defined in claim 8, wherein said second coil is intertwined with said first coil.

17. The stent as defined in claim 5, wherein said first coil and said second coil include first and second ends, said first ends of said first and second coils being connected together, said second ends of said first and second coils being disconnected from one another.

18. The stent as defined in claim 6, wherein said first coil and said second coil include first and second ends, said first ends of said first and second coils being connected together, said second ends of said first and second coils being disconnected from one another.

19. The stent as defined in claim 8, wherein said first coil and said second coil include first and second ends, said first ends of said first and second coils being connected together, said second ends of said first and second coils being disconnected from one another.

20. The stent as defined in claim 13, wherein said first coil and said second coil include first and second ends, said first ends of said first and second coils being connected together, said second ends of said first and second coils being disconnected from one another.

21. The stent as defined in claim 16, wherein said first coil and said second coil include first and second ends, said first ends of said first and second coils being connected together, said second ends of said first and second coils being disconnected from one another.

22. The stent as defined in claim 5, wherein said teeth on said first and second coils are design to enable said first and second coils to a move relative to one another when said coils are expanded and to inhibit said first and second coils to a move relative to one another when said coils are contracted.

23. The stent as defined in claim 6, wherein said teeth on said first and second coils are design to enable said first and second coils to a move relative to one another when said coils are expanded and to inhibit said first and second coils to a move relative to one another when said coils are contracted.

24. The stent as defined in claim 8, wherein said teeth on said first and second coils are design to enable said first and second coils to a move relative to one another when said coils are expanded and to inhibit said first and second coils to a move relative to one another when said coils are contracted.

25. The stent as defined in claim 13, wherein said teeth on said first and second coils are design to enable said first and second coils to a move relative to one another when said coils are expanded and to inhibit said first and second coils to a move relative to one another when said coils are contracted.

26. The stent as defined in claim 16, wherein said teeth on said first and second coils are design to enable said first and second coils to a move relative to one another when said coils are expanded and to inhibit said first and second coils to a move relative to one another when said coils are contracted.

27. The stent as defined in claim 20, wherein said teeth on said first and second coils are design to enable said first and second coils to a move relative to one another when said coils are expanded and to inhibit said first and second coils to a move relative to one another when said coils are contracted.

28. The stent as defined in claim 21, wherein said teeth on said first and second coils are design to enable said first and second coils to a move relative to one another when said coils are expanded and to inhibit said first and second coils to a move relative to one another when said coils are contracted.

29. The stent as defined in claim 5, wherein said teeth on said first and second coils are angularly offset with respect to a perpendicular to a longitudinal axis of each of said coils.

30. The stent as defined in claim 27, wherein said teeth on said first and second coils are angularly offset with respect to a perpendicular to a longitudinal axis of each of said coils.

31. The stent as defined in claim 28, wherein said teeth on said first and second coils are angularly offset with respect to a perpendicular to a longitudinal axis of each of said coils.

32. The stent as defined in claim 5, wherein said coil system including a third and fourth coil, said third coil turning in a first direction and said fourth coil turning in a second direction opposite said first direction, said third coil including a plurality of teeth, said fourth coil including a plurality of teeth, at least one of said teeth on said third coil designed to engage at least one of said teeth on said fourth coil.

33. The stent as defined in claim 30, wherein said coil system including a third and fourth coil, said third coil turning in a first direction and said fourth coil turning in a second direction opposite said first direction, said third coil including a plurality of teeth, said fourth coil including a plurality of teeth, at least one of said teeth on said third coil designed to engage at least one of said teeth on said fourth coil.

34. The stent as defined in claim 31, wherein said coil system including a third and fourth coil, said third coil turning in a first direction and said fourth coil turning in a second direction opposite said first direction, said third coil including a plurality of teeth, said fourth coil including a plurality of teeth, at least one of said teeth on said third coil designed to engage at least one of said teeth on said fourth coil.

35. The stent as defined in claim 32, wherein said coil system including a fifth and sixth coil, said fifth coil turning in a first direction and said sixth coil turning in a second direction opposite said first direction, said fifth coil including a plurality of teeth, said sixth coil including a plurality of teeth, at least one of said teeth on said fifth coil designed to engage at least one of said teeth on said sixth coil.

36. The stent as defined in claim 5, wherein said coil system is balloon expandable.

37. The stent as defined in claim 30, wherein said coil system is balloon expandable.

38. The stent as defined in claim 31, wherein said coil system is balloon expandable.

39. The stent as defined in claim 5, wherein said coil system is self expanding.

40. The stent as defined in claim 30, wherein said coil system is self expanding.

41. The stent as defined in claim 31, wherein said coil system is self expanding.

42. The stent as defined in claim 5, wherein said body portion is at least partially formed from a bio-degradable material.

43. The stent as defined in claim 30, wherein said body portion is at least partially formed from a bio-degradable material.

44. The stent as defined in claim 31, wherein said body portion is at least partially formed from a bio-degradable material.

45. The stent as defined in claim 5, wherein said body portion includes a pharmacological agent, is coated with a pharmacological agent, or combinations thereof.

46. The stent as defined in claim 30, wherein said body portion includes a pharmacological agent, is coated with a pharmacological agent, or combinations thereof.

47. The stent as defined in claim 31, wherein said body portion includes a pharmacological agent, is coated with a pharmacological agent, or combinations thereof.

48. The stent as defined in claim 5, wherein at least a portion of said body portion is formed by at least one MEM-based process.

49. The stent as defined in claim 30, wherein at least a portion of said body portion is formed by at least one MEM-based process.

50. The stent as defined in claim 31, wherein at least a portion of said body portion is formed by at least one MEM-based process.

* * * * *